United States Patent [19]

Scheinbaum

[11] Patent Number: 5,436,272

[45] Date of Patent: Jul. 25, 1995

[54] TREATMENT OF OBESITY

[75] Inventor: Monte L. Scheinbaum, Shreveport, La.

[73] Assignee: The Boots Company (USA), Inc., Shreveport, Ind.

[21] Appl. No.: 962,175

[22] Filed: Oct. 15, 1992

Related U.S. Application Data

[63] Continuation of Ser. No. 576,100, Aug. 31, 1990, abandoned, which is a continuation of Ser. No. 277,240, Nov. 19, 1988, abandoned.

[51] Int. Cl.$^6$ ............................................. A61K 31/135
[52] U.S. Cl. .................................... 514/646; 514/904; 514/910
[58] Field of Search ......................... 514/646, 904, 910

[56] References Cited

U.S. PATENT DOCUMENTS

| | | | |
|---|---|---|---|
| 4,443,449 | 4/1984 | Jeffery et al. | 514/255 |
| 4,522,828 | 6/1985 | Jeffery et al. | 514/646 |
| 4,746,680 | 5/1988 | Jeffery et al. | 514/646 |

(List continued on next page.)

FOREIGN PATENT DOCUMENTS

| | | | |
|---|---|---|---|
| 2184122 | 2/1988 | United Kingdom | A61K 31/135 |
| 8806444 | 9/1988 | WIPO | A61K 31/135 |

OTHER PUBLICATIONS

King et al 1988 110CA:33617z.
Buckett et al 1988 109CA:204745a.
Wurtman et al J. J. D-Fenfluramine selectively decreases carbohydrate but not protein intake in obese subjects. Int'l Journal of Obesity vol. 8, suppl. 1, 79–84 (1984).
Rockwell et al, W. J. K. Psychotropic drugs promoting weight gain: health risks and treatment implications. South Med. J. 76:1407–1412, (1983).
Fuller, R. W. Pharmacologic modification of serotonergic function: drugs for the study and treatment of psychiatric and other disorders. J. Clin. Psychiatry 47 (Suppl. 4): 4–8 (1986).
Paykel et al, E.S. Amitriptyline, weight gain and carbohydrate craving: a side effect. Br. J. Psychiatry 123: 501–507 (1973).
Nakra et al, B.R.S. Amitriptyline and weight gain: a biochemical and endrocrinological study. Current Med. Res. Opin. 4: 602–606 (1977).
Asberg et al, M. Therapeutic effects of serotonin uptake inhibitors in depression. J. Clin. Psychiatry 47 (Suppl. 4): 23–35. (1986).
Angel et al., "Anorectic Activities of Serotonin Uptake Inhibitors: Correlation With Their Potencies At Inhibiting Serotonin Uptake In Vivo and $^3$H-Mazindol Binding In Vitro;" Life Sciences, vol. 43, pp. 651–658; 1988.
Blundell, J. E., "Serotonin and Appetite", Neuropharmacology, vol. 23, No. 12B, pp. 1537–1551, 1984.
Luscombe et al., British J. Pharmacol., 1987, p. 575 (Proceedings Supplement) presented at British Pharmacol. Society, Oxford, Sep. 9–11, 1987, "Down-Regulation of Rat Cortical $\beta$-Adrenoceptors by the Putative Antidepressant BTS 54 524: Contribution of Metabolites".
Wynne et al., Abstracts, III World Conf. on Clin. Pharmacol. & Therapeutics, Stockholm, Jul. 27–Aug. 1, 1986, "The Effect of BTS 54 524, A Novel Antidepressant, on Monoamine Reuptake and Cardiovascular Parameters in Man".
Buckett et al., Collegium International Neuro-Psychopharmacologicum Dec. 14–17, 1986, p. 251, "The Pharmacology of BTS 54 524, a New Antidepressant Which Induces Rapid Noradrenergic Down-Regulation".

(List continued on next page.)

Primary Examiner—Marianne M. Cintins
Assistant Examiner—Russell Travers
Attorney, Agent, or Firm—Nikaido, Marmelstein, Murray & Oram

[57] ABSTRACT

N,N-dimethyl-1-[1-(4-chlorophenyl)cyclobutyl]-3-methylbutylamine hydrochloride is used in the treatment of obesity in humans.

8 Claims, No Drawings

U.S. PATENT DOCUMENTS

| | | | |
|---|---|---|---|
| 4,767,790 | 8/1988 | Jeffery et al. | 514/646 |
| 4,806,570 | 2/1989 | Jeffery et al. | 514/646 |
| 4,814,352 | 3/1989 | Jeffery et al. | 514/646 |

OTHER PUBLICATIONS

Buckett et al., British Pharmacol. Soc., Oral Communication, Dec. 19, 1986 "the Putative Antidepressant BTS 54 524 Rapidly and Potentially Down-Regulates Cortical β-Adrenoceptors in the Rat".

Buckett et al., British Pharmacol. Soc., Oral Communication, Dec. 19, 1986 "BTS 524, A Monoamine Uptake Inhibitor Exhibiting Potent Actions in Models Predictive of Potential Antidepressant Activity".

Luscombe et al., Int'l Symp on Antidepressants, Jerusalem, Apr. 1987, "The Putative Antidepressant BTS 54 524 Induces Rapid and Potent Down-Regulation of Cortical β-Adrenoceptors in the Rat: Contribution of Metabolites".

Buckett et al., New Concepts in Depression, vol. 2, pp. 167-172, "BTS 54 524—An Approach to a Rapidly Acting Antidepressant", 1987.

Buckett et al., Prog. Neuro-Psychopharmacol. & Biol. Psychiat. 1988, vol. 12 pp. 575-584, "The Pharmacology of Sibutramine Hydrochloride (BTS 54 524), a New Antidepressant which Induces Rapid Noradrenergic Down-Regulation".

King et al., Br. J. Clin. Pharmac, 1988, vol. 26, pp. 607-611, "Clinical pharmacology of sibutramine hydrochloride (BTS 54 524), a new antidepressant, in healthy volunteers".

Manna et al., Int. Clin. Psychopharmacol. 1989, Jan. 4, suppl. 1, pp. 81-88, Double-Blind Controlled Study on the Clinical Efficacy and Safety of Fluoxetine vs. Clomipramine in the Treatment of Major Depressive Disorders.

Fernstrom et al, M.H. Chronic imipramine treatment and weight gain. *Psychiatry Res* 17. 269-275 (1986).

Haskell et al, D.S. Doxepin or diazepam for anxious and anxious-depressed outpatients. *J. Clin. Psychiatry* 39: 135-139 (1978).

Feighner et al, J.P. Double-blind comparative trials of fluoxetine and doxepin in geriatric patients with major depressive disorder. *J. Clin. Psychiatry* 46: 20-25 (1985).

Nakra et al, B.R.S. Carbohydrate craving and weight gain with maprotiline. *Psychosomatics* 27: 376-381 (1986).

Orzack et al, M.H. Weight changes in antidepressants: a comparison of amitriptyline and trazodone. *Neuropsychobiol* 15: 28-30 (1986).

Levitt et al, A. J. The effect of desipramine on body weight in depression. *J. Clin. Psychiatry* 40: 27-28 (1987).

Wurtman et al, J.J. Drugs that enhance central serotonergic transmission diminished elective carbohydrate consumption by rats. *Life Sci* 24: 895-904 (1979).

Wurtman et al, J.J. Carbohydrate craving in obese people: supression by treatment affecting serotonergic transmission. *Int. J. Eat Disord* 1: 2-15 (1981).

Blundell et al, J. E. On the Mechanism of Action of Dexfenfluramine: Effect on Alliesthesia and Appetite Motivation in Lean and Obese Subjects. *Clinical Neuropharmacology* vol. 11, suppl 1 (1988) pp. S122-S134.

Rozen et al, R. Permanent Administration of d-Fenfluramine in Rats: Paradoxical Effects. *Clinical Neuropharmacology* vol. 11, Suppl 1 (1988) pp. S105-S112.

Campbell et al, D. B. Factors that may effect the reduction of hunger and body weight following d-fenfluramine administration. *Clinical Neuropharmacology* vol. 11 Suppl (1988) pp. S160-S172.

Turner P. Human Implications of Animal Experiments—Lessons from Dexfenfluramine. *Clinical Neuropharmacology* vol. 11 Suppl 1 (1988) pp. S113-S120.

Richelson et al, E. Blockade by antidepressants and related compounds of biogenic amine uptake into rat brain synaptosomes: most antidepressants selectively block norepinephrine uptake. *Eur. J. Pharmcol.* 104: 277-286 (1984).

Hall et al, H. Effects of antidepressant drugs on different receptors in the brain. *Eur. J. Pharmacol.* 70: 393-407 (1981).

Richardson et al, J. W. Antidepressants: a clinical update for medical practitioners. *Mayo Clin. Proc.* 59: 330-337 (1984).

Richelson et al, E. Antagonism by Antidepressants of neurotransmitter receptors of normal human brain *in vitro*. *J. Pharmacol. Exp. Ther.* 230: 94-102 (1984).

Berken et al, G. H. Weight gain: a side effect of tricyclic antidepressants. *J Affective Dis.* 7: 133-138 (1984).

(List continued on next page.)

OTHER PUBLICATIONS

Robinson et al, D. S. A comparison of trazodone, amoxapine, and maprotiline in the treatment of endogenous depression: results of a multicenter study. *Curr. Ther. Res. Clin. Exp.* 35: 549–560 (1984).

Stern et al, S. L. Lack of weight gain under desipramine. *Biol. Psychiatry* 22: 796–797 (1987).

Benfield et al, P. Fluoxetine. *Drugs* 32: 481–508 (1986).

Fernstrom et al, M. H. Resting metabolic rate is reduced in patients treated with antidepressants. *Biol Psychiatry* 20: 692–695 (1985).

Cheetham et al, S. C. Inhibition of [$^3$H]-paroxetine binding by sibutramine, its metabolites and other antidepressants correlates with inhibition of [$^3$H]-5-HT uptake. *Brit. J. Pharm* vol. 101 515P (1990).

Luscombe et al, G. The contribution of metabolites to the rapid and potent down-regulation of rat cortical $\beta$-adrenoceptors by the putative antidepressant sibutramine hydrochloride. *Neuropharmacology* vol. 28 pp. 129–134 (1989).

Brady, Kathleen T. "Weight Gain Associated Wtih Psychotropic Drugs." *Southern Medical Journal*, vol. 82, No. 5 (May 1989), pp. 611–617.

Hall, John "Fluoxetine: Efficacy Against Placebo and by Dose-An Overview." *British Journal of Psychiatry*, suppl. 3, (1988), pp. 59–63.

Altamura et al, A. C. "the Evidence of 20 mg a day of Fluoxetine as the Optimal Dose in the Treatment of Depression." *British Journal of Psychiatry*, suppl. 3, (1988), pp. 109–112.

Sommi et al, R. W. "Fluoxetine: A Serotonin-specific, Second-generation Antidepressant." *Pharmacotherapy*, vol. 7, No. 1 (1987), pp. 1–15.

Ferguson, James M. "Fluoxetine-Induced Weight Loss in Overweight, Nondepressed Subjects." *Am J Psychiatry*, vol. 143, No. 11 (1986), pp. 1496.

Stuppäck et al, Ch. "First Results of an Open Phase II Study with the Antideprssant Paroxetine." *Pharmacopsychiat.* (1988), pp. 369–370.

Warrington et al, S. J. "Cardiovascular (ECG and systolic time intervals) and anticholinergic effects of repeated doses of femoxetine—a comparison with amitriptylne and placebo in healthy men." *Br. J. clin. Pharmac.* No. 27, (1989), pp. 343–351.

Bitsch et al, Martin "Femoxetine in the Treatment of Obese Patients in General Practice." *International Journal of Obsesity*, vol. 11, (1987), pp. 183–190.

Cassano et al, Giovanni B. "Use of Standardized Documentation System (BLIPS/BDP) in the Conduct of a Multicenter International Trial Comparing Fluvoxamine, Imipramine, and Placebo." *Psychopharmacology Bulletin*, vol. 22, No. 1, (1986), pp. 52–58.

Abell et al, C. A. "Placebo controlled Double-Blind Trial of Fluvoxamine Maleate in the Obese." *Journal of Psychosmatic Research*, vol. 30, No. 2, (1986), pp. 143–146.

O'Rourke, et al, Dermot, M. D. "Treatment of Seasonal Depression With d-Fenfluramine." *J Clin Psychiatry*, vol. 50, No. 9, (Sep. 1989), pp. 343–347.

Guy-Grand, Bernard "International Trial of Long-Term Dexfenfluramine in Obesity." *The Lancet*, (Nov. 11, 1989), pp. 1142–1144.

Guy-Grand, Bernard, J. P. "Place of Dexfenfluramine in the Management of Obesity." *Clinical Neuropharmacology*, vol. 11, suppl. 1, (1988), pp. S216–S223.

Finer et al, N. "Effect of 6 Months Therapy with Dexfenfluramine in Obese Patients: Studies in the United Kingdom." *Clinical Neuropharmacology*, vol. 11, suppl. 1, (1988), pp. S179–S186.

Enzi et al, G. "Efficacy and Safety of Dexfenfluramine in Obese Patients: A Multicenter Study." *Clinical Neuropharmacology*, vol. 11, suppl. 1, (1988), pp. S173–S178.

Weintraub et al, Michael MD "A Double-blind Clinical Trial in Weight Control." *Arch Intern Med*, vol. 144, (Jun. 1984), pp. 1143–1148.

Garattini et al, S. "Reduction of Food Intake by Manipulation of Central Serotonin." *British Journal of Psychiatry*, vol. 155, suppl. 8, (1989), pp. 41–51.

Buckett et al., Prog. Neuro-Phychopharmacol and Biol Phychiat 1988, 12, 575–584.

Bernstein (Annals New York Academy of Sciences, 499 (1987) pp. 203–225).

Int. J. Obesity 11 Supplement 3 (1987) pp. 163–170 (Ferguson et al.), pp. 185–190 (Levine et al), pp. 191–199 (Zerbe).

TREATMENT OF OBESITY

This application is a continuation of application Ser. No. 576,100 filed Aug. 31, 1990, now abandoned, which was a continuation of U.S. Ser. No. 277,240, filed Nov. 29, 1988, now abandoned.

This invention relates to the medical treatment of obesity.

According to the present invention there is provided a method of treating obesity in which a therapeutically effective amount of N,N-dimethyl-1[1-(4-chlorophenyl)cyclobutyl]-3-methylbutylamine hydrochloride is administered in conjunction with a pharmaceutically acceptable diluent or carrier.

The use of N,N-dimethyl-1-[1-(4-chlorophenyl)-cyclobutyl]-3-methylbutylamine hydrochloride in the treatment of depression is described in British Patent Specification 2098602 and the use of N,N-dimethyl-1-[1-(4-chlorophenyl)cyclobutyl]-3-methylbutylamine hydrochloride in the treatment of Parkinson's disease is described in published PCT application WO 88/06444. A particularly preferred form of this compound is N,N-dimethyl-1-[1-(4-chlorophenyl)cyclobutyl]-3-methylbutylamine hydrochloride monohydrate (sibutramine hydrochloride) which is described in European Patent Application 230742.

The therapeutically active compound may be administered in any of the known pharmaceutical dosage forms for example solid dosage forms such as tablets or capsules or liquid dosage forms for example those forms intended for oral or parenteral administration. The amount of the compound to be administered will depend on a number of factors including the age of the patient, the severity of the condition and the past medical history of the patient and always lies within the sound discretion of the administering physician but it is generally envisaged that the dosage of the compound to be administered will be in the range 0.1 to 50 mg preferably 1 to 30 mg per day given in one or more doses.

The ability of sibutramine hydrochloride to cause weight reduction in humans has been demonstrated by the following trials.

TRIAL 1

39 male healthy volunteer subjects were treated in 3 groups:

Group 1

15 subjects were given 2.5 mg sibutramine hydrochloride per day for the first two weeks of the trial, followed by 5 mg sibutramine hydrochloride per day for the remaining four weeks of the trial.

Group 2

15 subjects were given 5 mg sibutramine hydrochloride per day for the first two weeks of the trial, followed by 10 mg sibutramine hydrochloride per day for the remaining four weeks of the trial.

Group 3

9 subjects were given a placebo containing no sibutramine hydrochloride.

The subjects were treated with a single dose of sibutramine hydrochloride or placebo taken each morning of the trial. The weight of each subject was taken at the commencement of treatment and after six weeks. The weight of each subject (in kgs) at the start and the change in weight (in kgs) over the six week trial period is given in Table 1 below.

TABLE 1

| | weight at start | weight change |
|---|---|---|
| | Group 1 given 2.5–5 mg | |
| | 71.4 | −3.2 |
| | 90.5 | −4.1 |
| | 74.1 | −2.3 |
| | 71.4 | −2.3 |
| | 102.7 | −7.2 |
| | 74.5 | −2.9 |
| | 78.2 | −4.6 |
| | 84.1 | 0 |
| | 63.6 | −0.2 |
| | 81.4 | −2.3 |
| | 73.6 | −3.6 |
| | 87.7 | −2.2 |
| | 70.0 | −4.1 |
| | 105.9 | +0.5 |
| | 85.0 | −0.9 |
| mean | 80.94 ± 11.99 | −2.63 ± 2.01 |
| | Group 2 given 5–10 mg | |
| | 76.4 | −3.9 |
| | 83.6 | −1.8 |
| | 73.2 | −1.4 |
| | 67.3 | −2.3 |
| | 79.1 | 0 |
| | 78.0 | −2.2 |
| | 83.6 | −6.3 |
| | 76.8 | −5.7 |
| | 69.5 | −1.3 |
| | 71.8 | −3.6 |
| | 82.7 | −5.0 |
| | 75.0 | −1.4 |
| | 75.9 | −3.2 |
| | 89.8 | −3.4 |
| | 68.2 | −1.8 |
| mean | 76.73 ± 6.34 | −2.89 ± 1.78 |
| | Group 3 given placebo | |
| | 78.1 | −1.1 |
| | 75.9 | −0.4 |
| | 77.3 | −0.3 |
| | 76.4 | −1.9 |
| | 81.8 | −0.7 |
| | 60.2 | +3.0 |
| | 67.3 | −2.1 |
| | 65.0 | −1.8 |
| | 73.6 | +3.7 |
| mean | 72.84 ± 7.09 | −0.18 ± 2.11 |

TRIAL 2

56 subjects who had been diagnosed as suffering from depression were treated in two groups. A first group (Group 1) of 26 subjects were treated with 10 mg of sibutramine hydrochloride per day for the first two weeks of the trial and then with 20 mg of sibutramine hydrochloride per day for a further period of four weeks. The second group (Group 2) were given a placebo containing no sibutramine hydrochloride every day throughout the trial. The subjects were treated with a single dose of sibutramine hydrochoride or placebo taken each morning of the trial. The weight of each subject was taken at the commencement of the trial and after six weeks. The weight of each subject (in kgs) at the start and the change in weight (in kgs) over the six week period are given below in Table 2.

TABLE 2

| weight at start | weight change |
|---|---|
| Group 1 | |
| 53.6 | −1.1 |
| 59.5 | −1.6 |
| 81.3 | +1.4 |
| 84 | −3.1 |

TABLE 2-continued

| | weight at start | weight change |
|---|---|---|
| | 57.3 | −0.3 |
| | 78.2 | −2.3 |
| | 86.4 | −5.0 |
| | 78.0 | −5.3 |
| | 89.8 | −0.8 |
| | 93.5 | −0.6 |
| | 64.5 | −0.4 |
| | 71.8 | −5.0 |
| | 81.8 | +3.2 |
| | 84.5 | −2.2 |
| | 103.2 | −3.2 |
| | 55.5 | −1.9 |
| | 80.9 | −1.4 |
| | 67.0 | −1.3 |
| | 87.2 | −4.8 |
| | 92.9 | 0 |
| | 96.5 | −0.9 |
| | 60.2 | −2.2 |
| | 68.9 | −0.9 |
| | 84.7 | 0.5 |
| | 94.7 | −1.8 |
| | 93.3 | −0.7 |
| mean | 78.4 ± 13.2 | −1.6 ± 2.0 |
| Group 2 | | |
| | 79.5 | +0.5 |
| | 84.4 | +1.5 |
| | 85.0 | −1.6 |
| | 89.7 | +2.1 |
| | 58.2 | −5.4 |
| | 79.5 | −0.9 |
| | 79.5 | 0 |
| | 97.5 | +6.1 |
| | 66.7 | +0.4 |
| | 59.5 | −0.4 |
| | 68.6 | +1.9 |
| | 70.9 | +0.9 |
| | 88.6 | +3.2 |
| | 89.1 | +1.3 |
| | 67.7 | −0.4 |
| | 78.2 | −1.8 |
| | 65.5 | +0.4 |
| | 68.1 | +2.1 |
| | 74.8 | +1.8 |
| | 86.4 | +0.8 |
| | 88.0 | −0.6 |
| | 99.2 | +1.9 |
| | 102.4 | +1.3 |
| | 68.9 | −0.5 |
| | 78.8 | 0 |
| | 79.3 | +2.2 |
| | 85.6 | +0.9 |
| | 97.4 | −1.6 |
| | 46.2 | −0.5 |
| | 70.2 | +0.5 |
| mean | 78.4 ± 13.2 | +0.5 ± 2.0 |

I claim:

1. A method of treating obesity in humans which comprises administering by oral or parenteral means to a human in need thereof a therapeutically effective amount of N,N-dimethyl-1-[1-(4-chlorophenyl) cyclobutyl]-3-methylbutylamine hydrochloride in conjunction with a pharmaceutically acceptable diluent or carrier.

2. A method as claimed in claim 1 wherein N,N-dimethyl-1-[1-(4-chlorophenyl)cyclobutyl]-3-methylbutylamine hydrochloride is administered in the form of its monohydrate.

3. Method of claim 1, wherein the N,N-dimethyl-1-[1-(4-chlorophenyl) cyclobutyl]-3-methylbutylamine hydrochloride is administered orally.

4. Method of claim 1, wherein the N,N-dimethyl-1-[1-(4-chlorophenyl) cyclobutyl]-3-methylbutylamine hydrochloride is administered parenterally.

5. Method of claim 1, wherein the N,N-dimethyl-1-[1-(4-chlorophenyl) cyclobutyl]-3-methylbutylamine hydrochloride is administered in an amount of from about 0.1 to about 50 mg per day.

6. Method of claim 5, wherein the amount is 1 to 30 mg per day.

7. Method of claim 1, wherein the N,N-dimethyl-1-[1-(4-chlorophenyl) cyclobutyl]-3-methylbutylamine hydrochloride is administered in an amount from 2.5 to 20mg per day.

8. Method of claim 1, wherein the N,N-dimethyl-1-[1-(4-chlorophenyl) cyclobutyl]-3-methylbutylamine hydrochloride is administered in an amount of about 10mg per day.

* * * * *